United States Patent
Doerr

(10) Patent No.: US 8,558,514 B2
(45) Date of Patent: Oct. 15, 2013

(54) DETECTOR FOR ELECTROMAGNETIC FIELDS

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 537 days.

(21) Appl. No.: 12/957,432

(22) Filed: Dec. 1, 2010

(65) Prior Publication Data

US 2011/0148365 A1 Jun. 23, 2011

Related U.S. Application Data

(60) Provisional application No. 61/288,853, filed on Dec. 22, 2009.

(51) Int. Cl.
*H02J 7/04* (2006.01)
*H02J 7/16* (2006.01)

(52) U.S. Cl.
USPC .......................... 320/162; 320/166; 320/167

(58) Field of Classification Search
USPC .......................... 320/162, 166–167
See application file for complete search history.

(56) References Cited

U.S. PATENT DOCUMENTS

| | | | |
|---|---|---|---|
| 5,251,624 A * | 10/1993 | Bocek et al. ............... | 607/6 |
| 6,522,920 B2 | 2/2003 | Silvian et al. | |
| 7,509,167 B2 | 3/2009 | Stessman | |
| 2002/0072769 A1 | 6/2002 | Silvian et al. | |
| 2007/0191914 A1* | 8/2007 | Stessman ............... | 607/63 |
| 2008/0071168 A1 | 3/2008 | Gauglitz et al. | |

FOREIGN PATENT DOCUMENTS

EP 0670170 9/1995

OTHER PUBLICATIONS

European Search Report Dated Mar. 31, 2011 (7 pages).

* cited by examiner

*Primary Examiner* — Samuel Berhanu
(74) *Attorney, Agent, or Firm* — ARC IP Law, PC; Joseph J. Mayo

(57) ABSTRACT

A battery-powered electrical device is disclosed, which may be implemented as an implantable medical device, wherein the device contains at least one battery voltage monitoring unit which is designed to monitor a voltage profile at a battery during the charging of a capacitor, via a transformer in a charging circuit, and which on the basis of the voltage characteristic is able to specify a magnetic presaturation of the transformer, and one control unit which terminates the charging process whenever a predefined threshold value for the magnetic presaturation of the transformer is exceeded.

13 Claims, 4 Drawing Sheets

DETECTOR FOR ELECTROMAGNETIC FIELDS

RELATED APPLICATION

This patent application claims the benefit of U.S. Provisional Patent Application No. 61/288,853, filed on Dec. 22, 2009, which is hereby incorporated by reference in its entirety.

TECHNICAL FIELD

The present disclosure is related to a method for detecting electromagnetic fields, in particular those which occur in imaging magnetic resonance tomography (MRT) or magnetic resonance imaging MRI) devices, and for battery-powered devices such as implantable medical devices.

BACKGROUND

Although MRI testing is becoming increasingly important in diagnostic medicine, it is contraindicated for some patients. Such contraindication may result from an active implanted medical device.

Besides possible heating effects of implants, in particular for small conductive structures (not addressed here), there are problems with erroneous identifications of events in the heart, including but not limited to ventricular fibrillation (VF), i.e., rapid disturbances in cardiac rhythm, and the high static magnetic fields and resulting magnetization of electrical components, in particular for active implants, including but not limited to implanted cardiac defibrillators/cardioverters, referred to below as ICD. However, other battery-powered devices may also be functionally impaired by electromagnetic fields, and cannot be used in environments having increased electromagnetic loads. The following prior art primarily addresses the problems with implanted medical devices (IMD).

U.S. Pat. No. 6,522,920 describes a system for protecting the inductively actuated high-voltage switches of an ICD in the delivery of shocks in a magnetic field. For this purpose monitoring is performed to determine whether sufficient gate voltage is present at the time of delivery of the shock. The monitoring is assessed by an evaluation of the secondary voltage of the inductive drivers.

For detection of a magnetic field it is known from US Patent Application Publication 2008/0071168 discloses providing an impedance measuring unit for detection of a magnetic field and an RLC (Resistor-Inductor-Capacitor) element, and to perform the detection by determining the inductance in the RLC component of the implanted device. This requires an additional or modified impedance measuring unit.

In addition, U.S. Pat. No. 7,509,167 describes the detection of a magnetic field by measuring the control times for actuating the high-voltage transformer for the primary side, or alternatively, measuring peak currents during a charging cycle. A disadvantage of the described system is that the control times must be measured very quickly, because they are in the μs to ns range; i.e., it is difficult to perform a direct current measurement due to the necessary measurement resistance, which would prolong the charging times for the high-voltage capacitor.

What is needed is a way is to provide magnetic field detection, in particular MRI detection, so that it is easy to implement.

SUMMARY

The object is achieved by use of a battery-powered electrical device (BED) having the claimed features. The BED includes at least one battery voltage monitoring unit for use in monitoring a voltage profile at a battery during the charging of a capacitor, via a transformer in a charging circuit, and on the basis of the voltage profile to specify a magnetic presaturation of the transformer, and at least one control unit which terminates charging the capacitor whenever a predefined threshold value for the magnetic presaturation of the transformer is exceeded.

The BED may or may not be a implanted medical device or a temporarily implanted medical device or an external medical device, e.g. a external defibrillator.

In one preferred embodiment, the exceedance of the threshold value for the magnetic presaturation of the transformer is detected by measuring a minimum battery voltage during charging.

It is also preferred to detect the exceedance of the threshold value for the magnetic presaturation of the transformer by measuring a maximum voltage gradient dU/dt at the start of charging.

The term "start of charging" is understood to mean the first seconds, preferably the first 200 ms, particularly preferably the first 100 ms, and also particularly preferably the first 10 ms, of a charging process.

In a further embodiment an exceedance of the threshold for the magnetic presaturation of the transformer is detected by measuring a maximum battery voltage difference before and during charging.

In a further embodiment, an exceedance of the threshold for the magnetic presaturation of the transformer is detected by measuring a minimum battery voltage during the charging and a maximum voltage difference before and during charging.

The charging current is preferably limited in such a way that the battery voltage is not less than a minimum value.

In a further embodiment it is preferred that when the charging process is terminated the charging circuit is deactivated for a first period of time. For example, the control unit may terminate the charging process when the threshold value for the presaturation of the transformer is reached or exceeded.

It is also preferred, that the charging circuit is deactivated by a series of time intervals. The first period of time for the deactivation of the charging circuit for consecutive charging terminations within a second specified period of time is shortened by means of the control unit and the battery voltage monitoring unit, in each case by a third specified period of time, wherein the period of time for the deactivation of the charging circuit is not less than a specified minimum value, and the first period of time for the deactivation of the charging circuit is restored after a fourth specified period of time.

It is preferred that the device may be placed in an MRI-safe state by programming. Programming may or may be not include remote programming.

It is also preferred that when an exceedance of the threshold value for the magnetic presaturation of the transformer is detected, this is notated in a diagnostic memory, and/or no episodes are recorded during an MRT test. This prevents an MRT session from overwriting the diagnostic data with artifacts.

"Remote programming" is understood to mean the programming of an IMD, wherein the IMD and the programming unit or units are spatially separated in such a way that the normally present near-field telemetry (<10 m) alone is not sufficient to bridge the spatial separation.

It is particularly preferred that the control unit terminates the charging process upon reaching or exceeding the threshold value for the presaturation of the transformer, and places the battery-powered electrical device in the MRI-safe state for a predeterminable period of time.

In a further embodiment, transition to the MRI-safe state is transmitted by telemetric remote monitoring, so-called "home monitoring." That is to say, when the MRI-safe state is switched on a signal or information is sent, directly or via at least one intermediate device, for example a patient device, to a central unit which processes or optionally relays the signal or information. If a connection to the central unit does not exist or cannot be established during switching on of the MRI-safe state, the signal or information is sent or transmitted at a later time, preferably as soon as a connection to the central unit exists or can be established.

Telemetric remote monitoring refers in general to the possibility of transmitting information or signals from an IMD to a remote unit to allow monitoring of the patient without a doctor's visit or hospitalization, for example by sending data from the implant via a service center to an attending physician.

It is preferred that the battery-powered electrical device is an implantable medical device (IMD).

It is particularly preferred that the IMD is an implantable defibrillator/cardioverter (ICD), which may or may not include an IMD for cardiac resynchronization in an ICD.

It is particularly preferred that an MRI-safe state includes the suppression of the delivery of high-voltage shocks.

It is likewise particularly preferred that an MRI-safe state includes patient dependent stimulation modes, e.g. suppression of the delivery of pacemaker stimulations, or delivery of asynchronous pacemaker pulses. The decision concerning the appropriate MRI-safe state may be made either in the programming of the IMD, or automatically in the programming of the IMD, or automatically in the detection of an MRI field, or automatically at predetermined times or during specific events or patient states.

Likewise advantageous is the combination with other methods for detecting electromagnetic fields, in particular MRI fields, and combination with different reactions to electromagnetic fields, in particular MRI fields. The following additional detection methods, among others, may advantageously be provided:

GMR sensors,
MagFETs,
Evaluation of induced currents in electrodes or antennas as indicator,
Detection of specific vibrations, or components designed as sensors for detection of vibrations induced by Lorentz forces, as indicator, and
Position sensors as indicator.

"Indicators" refer to methods and/or devices which allow conclusions to be drawn concerning the presence of electromagnetic interference fields.

In response to detected electromagnetic fields, in particular MRI fields, other reactions are possible, in addition to those previously mentioned, such as, but not limited to:

Remaining for a prolonged period of time in an MRI-safe state or a state that is insensitive to electromagnetic interference fields, Synchronization of electrical measurements (impedance measurements, for example) using field intensity minimum values occurring with periodic or pulsed electromagnetic fields, or synchronization of a stimulation using these same minimum values, and Emission of electromagnetic pulses for signaling that a medical device, in particular an implant, is present in the electromagnetic field, in particular for signaling to an MRI device, with the possibility of thus transmitting information as well as the interference and displaying same on the MRI screen.

It is further preferred that a position sensor is used for plausibility checking, and a positive MRI identification is made only when the position sensor reports a prone posture or another presettable posture, or both.

The position sensor is particularly preferably self-calibrating, the calibration taking place under presettable boundary conditions such as, but not limited to, times of day, and/or heart rate, and/or respiratory rate, and/or hemodynamic parameters, and activity detected by a motion sensor.

In addition to the embodiments described herein other alternative embodiments may include some or all of the disclosed features.

DESCRIPTION OF THE DRAWINGS

Several aspects of the disclosed technology are illustrated in FIGS. 1 through 4.

DETAILED DESCRIPTION

Figure 1:
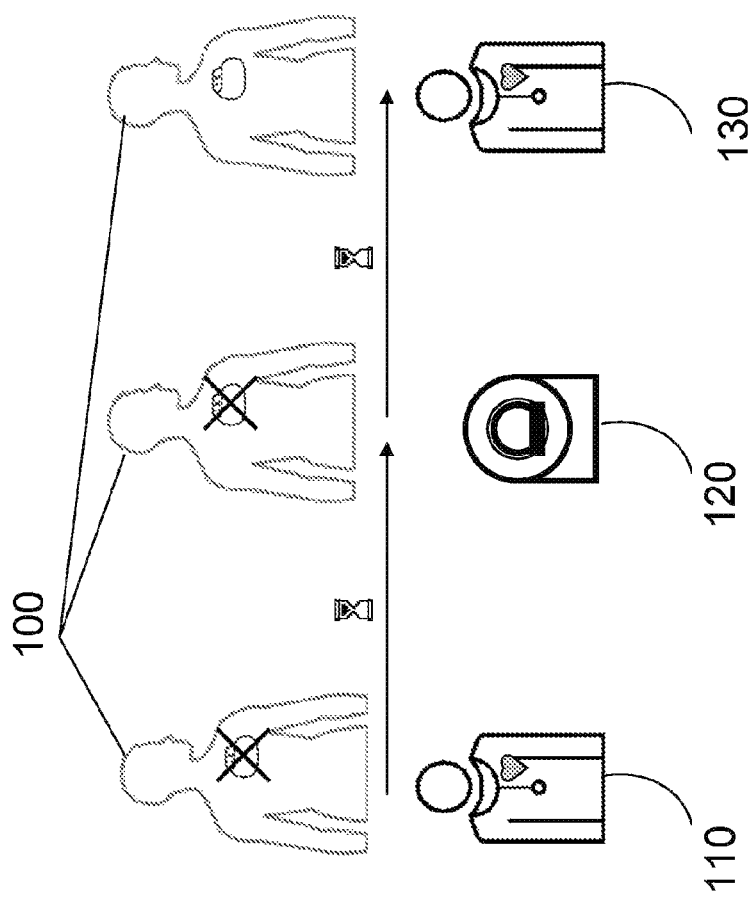
FIG. 1 shows a schematic illustration of the sequence of a prior art MRI test.

FIG. 1 describes the prior art, in which an ICD patient 100 receives follow-up care from a cardiologist 110 before a planned MRT test, and the ICD is switched off by the cardiologist 110. After a time delay of hours to days an MRT test is performed by a radiologist 120. After a further delay the patient is once again under the care of a cardiologist 130, who may or may not be the same as cardiologist 110, and the ICD is switched back on. Throughout the time interval from when cardiologist 110 switches off the ICD to when cardiologist 130 switches on the ICD, the patient is without the protection of the implanted defibrillator, and is essentially without rhythm monitoring. This residual risk is currently accepted in return for the benefits of the MRT test.

Figure 2:
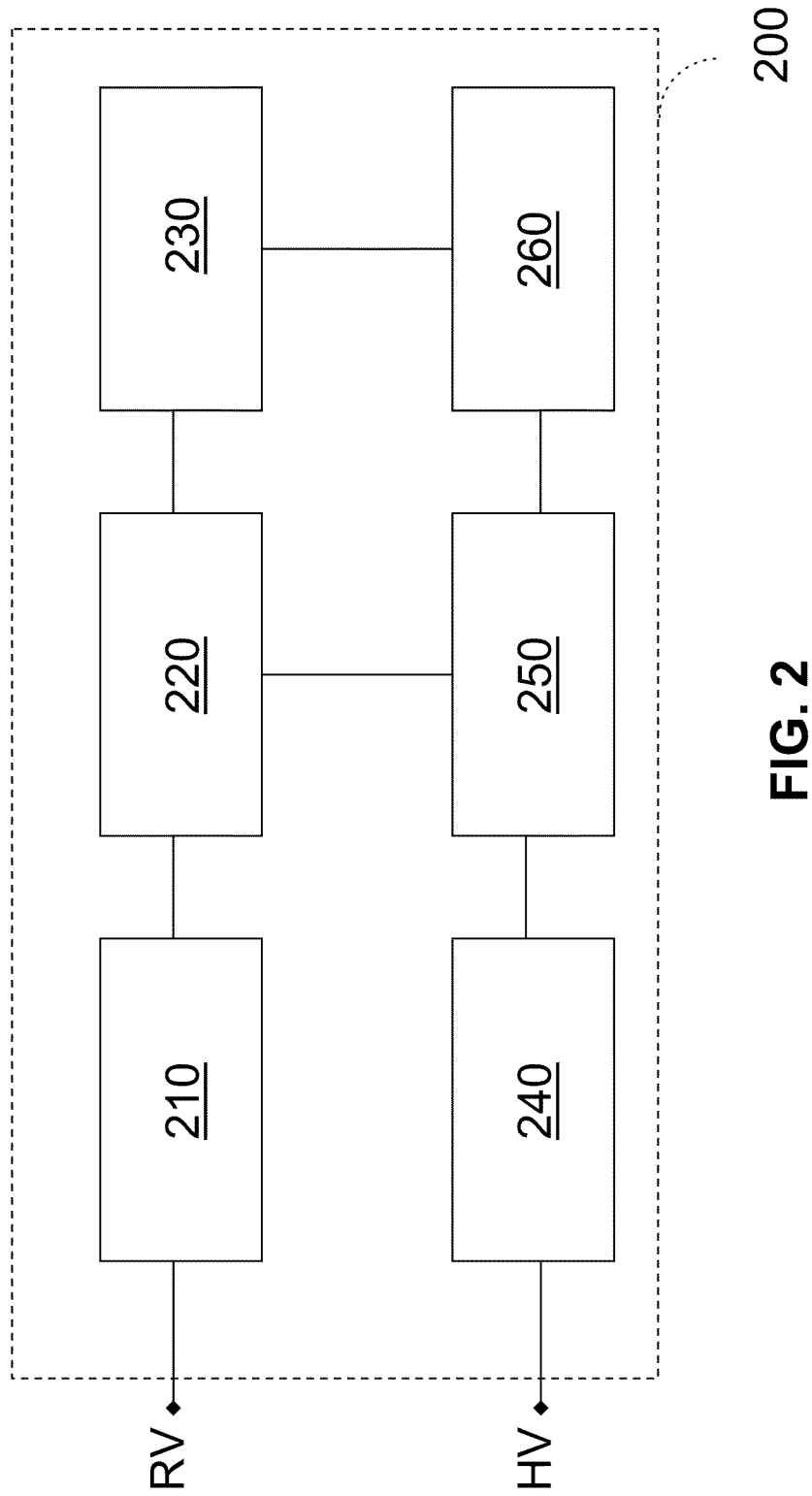
FIG. 2 shows a block diagram of an IMD together with an MRI detection unit.

FIG. 2 shows a block diagram for detecting an MRT magnetic field in an ICD 200. The electrode used for detection of ventricular fibrillation (VF), preferably a right ventricular (RV) electrode, is connected to the EKG signal sensing/rhythm classification and stimulation unit 210. This unit in turn is connected to a control unit, which starts the high-voltage charging circuit 250 for charging the high-voltage capacitors in the shock therapy unit 240 when VF is detected. This high-voltage charging circuit 250 includes a transformer which is sized so that it is completely or partially saturated by the magnetic field of an MRT. The charging circuit is supplied with power by a battery 260. According to this embodiment, this battery is connected to a battery voltage monitoring unit 230 which is designed in such a way that the dynamic battery voltage characteristics are detected during and after the start of charging and evaluated using comparative parameters. The battery voltage monitoring unit 230 is likewise connected to the control unit 220. When magnetic presaturation of the transformer for the charging circuit 250 is classified in the battery voltage monitoring unit 230, the charging process is terminated in the control unit, and the VF detection is suspended for a programmable period of time.

Figure 3:
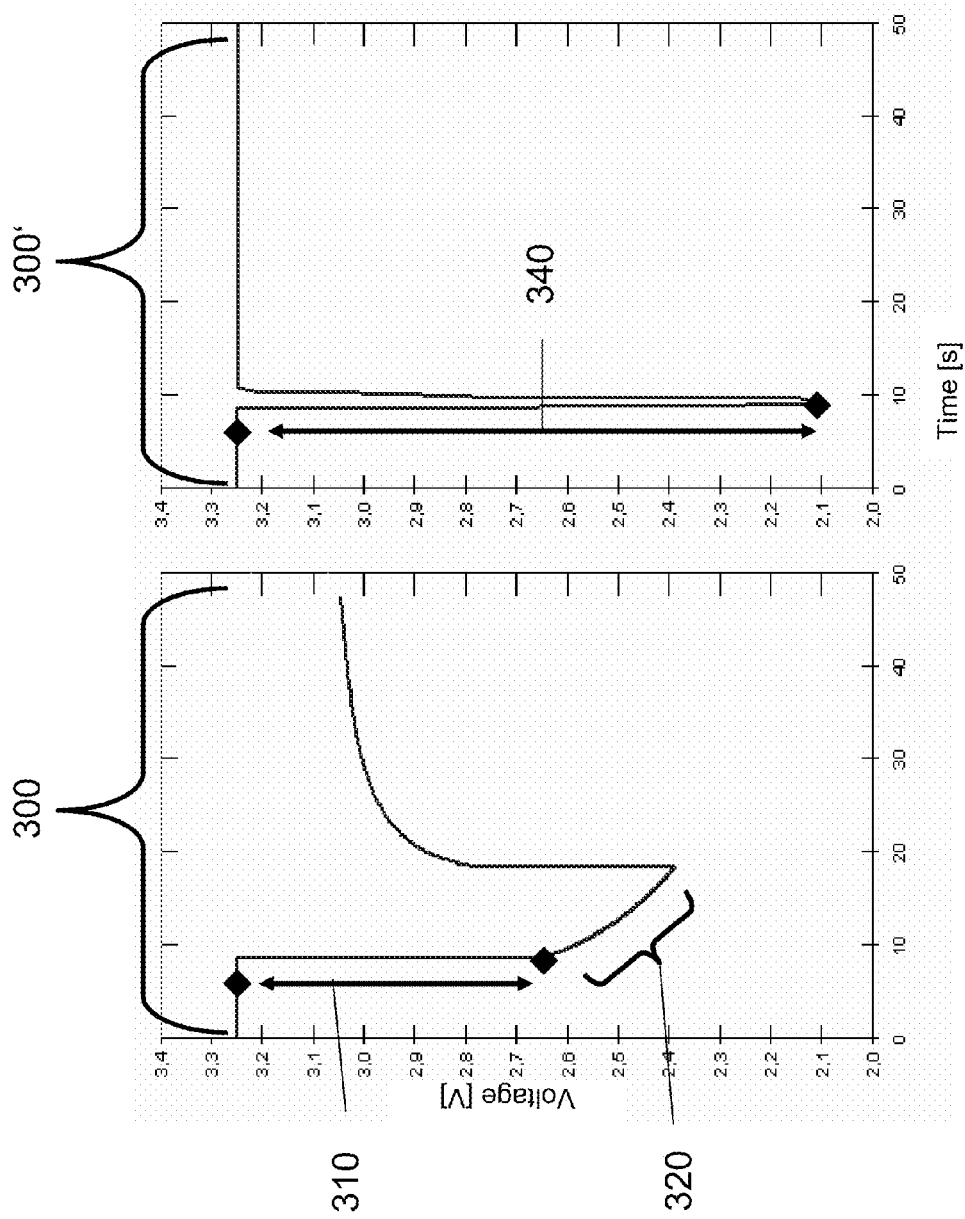
FIG. 3A shows a graphical illustration of the typical variation in battery voltage over time during charging of a shock capacitor.
FIG. 3B shows a graphical illustration of the typical variation in battery voltage over time during charging of a shock capacitor via a magnetically presaturated transformer core.

FIG. 3*a* shows, first of all, the typical variation in battery voltage 300 over time for charging of the shock capacitors. When the high-voltage charging circuit is connected, the battery voltage initially drops abruptly 310. This drop in voltage results from the internal battery resistance and the flowing charging current. During the charging of the shock capacitors the battery voltage drops further 320, typically within 5-10 seconds. This drop is dominated by the electrochemical systems of the battery.

FIG. 3*b* shows the voltage profile 300' for a strongly presaturated transformer core. In this case the battery voltage drops much lower 340 at the start of charging, since as the result of the saturation of the transformer the inductance thereof is lowered, and therefore the charging current increases significantly compared to a standard charging cycle. The voltage correspondingly drops more steeply at the same internal battery resistance. In the simplest implementation, the voltage monitoring unit 230 from FIG. 1 compares only the drop in voltage immediately after the start of charging with a programmed threshold value. If this value is exceeded, the charging process is immediately ended, and a signal is sent to a control unit or the VT/VF detection is blocked for a programmable period of time.

Figure 4:
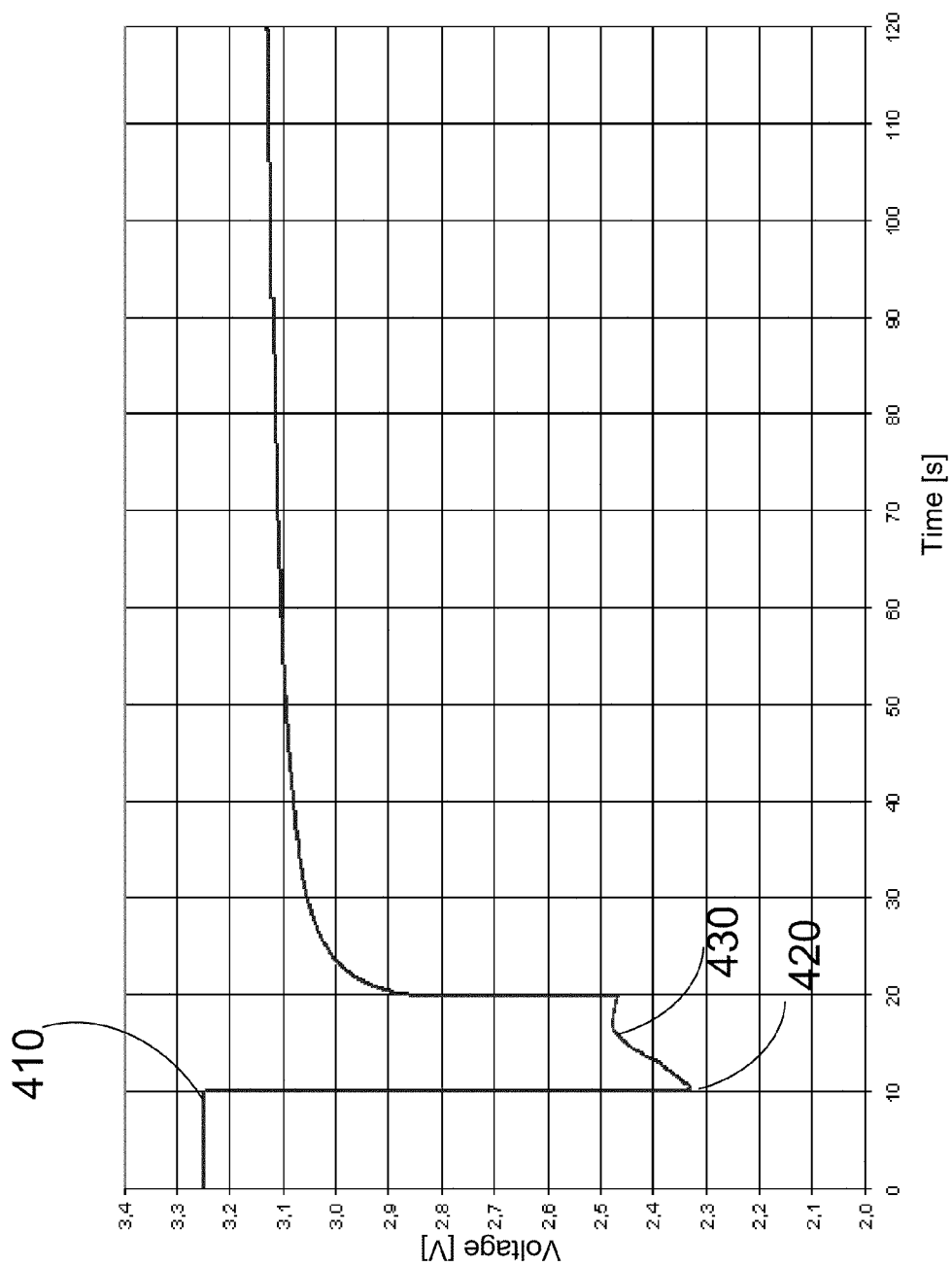
FIG. 4 shows a graphical illustration of the typical variation in battery voltage over time during charging of a shock capacitor having a partially discharged battery.

FIG. 4 shows a graphical illustration of a battery at the end of the operating period, with pronounced "voltage delay." The open circuit voltage 410 is not out of the ordinary. However, the battery voltage drops drastically at the start of charging 420, which may be confused with a saturated transformer. This is avoided by conducting an additional voltage measurement 430 at a later point in time. If this voltage is greater than the first value after the start of charging 420, a voltage delay, and not transformer saturation, is assumed. The second measurement is meaningful in particular when the implant has reached at least the second half of its expected operating time and has a silver vanadium oxide (SVO) battery.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A battery-powered electrical device, comprising:
a battery voltage monitoring unit configured to
monitor a voltage profile at a battery during charging of a capacitor, via a transformer in a charging circuit, and
specify a magnetic presaturation of the transformer based on the voltage profile; and
a control unit configured to terminate charging of the capacitor whenever a predefined threshold value of the magnetic presaturation of the transformer is reached or exceeded;
wherein the device is configured to be placed in an MRI-safe state by programming; and
wherein the control unit is further configured to place the battery-powered electrical device in the MRI-safe state for a prescribed period of time.

2. The battery-powered electrical device according to claim 1, wherein the exceedance of the threshold value of the magnetic presaturation of the transformer is configured to be detected by measuring a minimum battery voltage during charging.

3. The battery-powered electrical device according to claim 1, wherein the exceedance of the threshold value of the magnetic presaturation of the transformer is configured to be detected by measuring a maximum battery voltage gradient dU/dt at a start of the charging.

4. The battery-powered electrical device according to claim 1, wherein the exceedance of the threshold of the magnetic presaturation of the transformer is configured to be detected by measuring a maximum voltage difference before and during charging.

5. The battery-powered electrical device according to claim 1, wherein the exceedance of the threshold of the magnetic presaturation of the transformer is configured to be detected by measuring a minimum battery voltage during charging, and a maximum voltage difference before and during charging.

6. The battery-powered electrical device according to claim 1, wherein a charging current when charging is configured to be limited such that the battery voltage is not less than a minimum value.

7. The battery-powered electrical device according to claim 1, wherein when charging is terminated, the charging circuit is configured to be deactivated for a first period of time.

8. The battery-powered electrical device according to claim 7, wherein the charging circuit is deactivated by a series of time intervals.

9. The battery-powered electrical device according to claim 1, wherein transition to the MRI-safe state is configured to be transmitted by telemetric remote monitoring.

10. The battery-powered electrical device according to claim 1, wherein the device is an implantable medical device (IMD).

11. The battery-powered electrical device according to claim 10, wherein the IMD is an implantable defibrillator/cardioverter (ICD).

12. The battery-powered electrical device according to claim 11, wherein said MRI-safe state includes suppression of delivery of high-voltage shocks.

13. The battery-powered electrical device according to claim 11, wherein said MRI-safe state includes patient dependent stimulation modes.

* * * * *